United States Patent [19]

Nickolson et al.

[11] 4,025,563
[45] May 24, 1977

[54] NOVEL D-HOMO STEROIDS

[75] Inventors: Robert C. Nickolson; Ulrich Kerb; Rudolf Wiechert, all of Berlin, Germany

[73] Assignee: Schering Aktiengesellschaft, Berlin & Bergkamen, Germany

[22] Filed: Sept. 2, 1975

[21] Appl. No.: 609,706

[30] Foreign Application Priority Data

Sept. 4, 1974 Germany .......................... 2442615

[52] U.S. Cl. ...................... 260/586 E; 260/488 B; 424/311; 424/331
[51] Int. Cl.² ........................................ C07C 49/48
[58] Field of Search ................... 260/586 E, 488 B; 424/311, 331

[56] References Cited

UNITED STATES PATENTS 2,860,158  11/1958  Clinton ........................ 260/488 B

FOREIGN PATENTS OR APPLICATIONS 2,314,592  1973  Germany ...................... 260/586 E Primary Examiner—Gerald A. Schwartz
Attorney, Agent, or Firm—Millen & White

[57] ABSTRACT

D-homo steroids of the formula

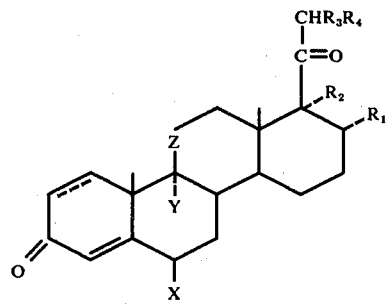

wherein X is H, F or CH₃; Y is H, F or Cl; Z is CH₂, CO, β-HOCH₂, β-AcOCH₂ or, when Y is Cl, also β-FCH₂ or β-ClCH₂; R₁ is H or CH₃, R₂ is H, OH or AcO; and one of R₃ and R₄ is H and the other is OH or alkoxy or both are O, possess anti-inflammatory activity.

15 Claims, No Drawings

NOVEL D-HOMO STEROIDS

BACKGROUND OF THE INVENTION

This invention relates to novel D-homo steroids and to processes for their production.

The novel D-homo steroids of this invention are those of general Formula I

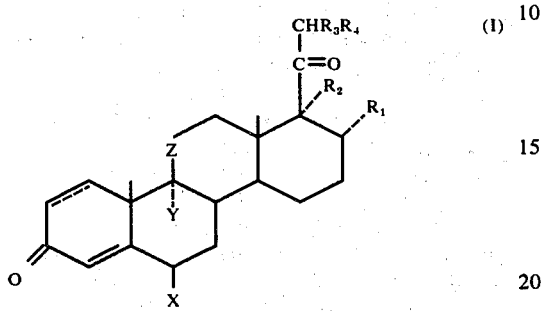

wherein
the $===$ a single bond or a double bond;
X is a hydrogen atom, a fluorine atom, or methyl;
Y is a hydrogen atom, a fluorine atom or a chlorine atom;
Z is a methylene, carbonyl, β-hydroxymethylene, β-alkanoyloxymethylene or, when Y is a chlorine atom, also β-fluoromethylene or a β-chloromethylene;
$R_1$ is a hydrogen atom or methyl;
$R_2$ is a hydrogen atom, a hydroxy, or an alkanoyloxy; and
one of $R_3$ and $R_4$ is a hydrogen atom and the other is hydroxy or lower alkoxy or collectively $R_3$ and $R_4$ are an oxo oxygen atom.

In another composition aspect this invention relates to pharmaceutical compositions comprising an antiinflammatorily effective amount per unit dosage of at least one D-homo steroid of this invention in admixture with a pharmaceutically acceptable carrier.

In process aspects, this invention relates to processes for the production and use of the D-homo steroids of this invention.

DETAILED DISCUSSION

Examples of alkanoyl when Z is β-alkanoyloxymethylene and when $R_2$ is alkanoyloxy are preferably those of a straight-chain alkanoic acid, i.e., an n-alkanecarboxylic acid, e.g., of 1–8 carbon atoms, such as, for example, formic acid, acetic acid, propionic acid, butyric acid and caproic acid.

Lower alkoxy $R_3$ and $R_4$ groups are preferably alkoxy of 1–4 carbon atoms, such as, for example, methoxy, ethoxy, propoxy, and butoxy.

Examples of contemplated classes of compounds of this invention are those wherein:

1a: $R_3$ and $R_4$ collectively are carbonyl;
1b: one of $R_3$ and $R_4$ is a hydrogen atom and the other is hydroxy;
1c: $R_1$ is H, especially those of (a) and (b);
1d: $R_1$ is $CH_3$, especially those of (a) and (b);
1e: $R_2$ is OH, especially those of (a) and (b);
1f: $R_2$ is H, especially those of (a), (b), (c) and (d);
1g: $===$ is a double bond, especially those of (a), (b), (c), (d), (e) and (f);
1h: $===$ is a single bond, especially those of (a), (b), (c), (d), (e), and (f);
1i: Z is β-hydroxymethylene, especially those of (a), (b), (c), (d), (e) and (f);
1j: Z is carbonyl, especially those of (a), (b), (c), (d), (e) and (f); and
1k: Z is methylene, especially those of (a), (b), (c), (d), (e) and (f).

In a process aspect, this invention relates to a process for the production of the novel D-homo steroids of Formula I wherein:

(a) a D-homo steroid of the general Formula II

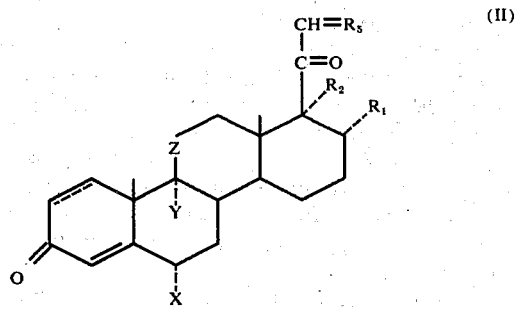

wherein
$===$, X, Y, Z, $R_1$ and $R_2$ have the values given for Formula I and
$R_5$ is a group convertable into an aldehyde group or an acetal thereof, is converted into an aldehyde group or an acetal thereor; or (b) a D-homo steroid of general Formula I saturated in the 1,2-position ($===$ is a single bond) is dehydrogenated to a corresponding $\Delta^{1,4}$-D-homo steroid of general Formula I; or (c) an epoxide of general Formula III

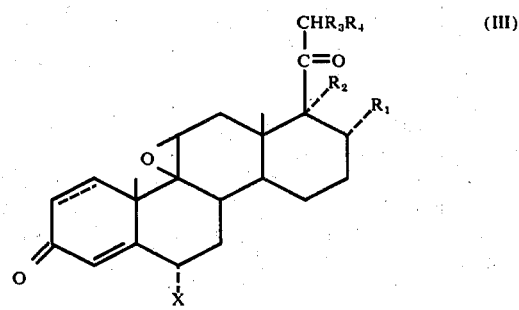

wherein $===$, X, $R_1$, $R_2$, $R_3$ and $R_4$ have the values given above for Formula I, is opened with hydrogen fluoride or hydrogen chloride to give a D-homo steroid of general Formula I wherein Z is β-hydroxymethylene group and Y is a fluorine or chlorine atom; or (d) a compound of general Formula IV

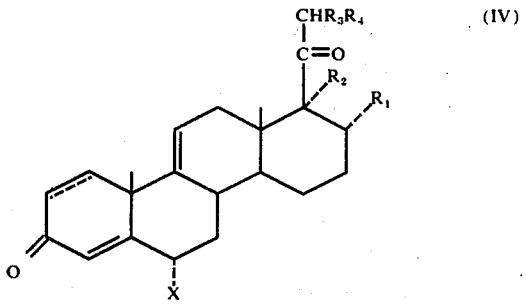

wherein ═, X, R₁, R₂, R₃ and R₄ have the values given above for formula I, is reacted hypochlorous acid, chlorine, or a mixture of fluorine and chlorine to give a D-homo steroid of general Formula I wherein Y is a chlorine atom; and, optionally thereafter, a free hydroxy group is esterified.

The process of this invention can be conducted, for example, as described in German Published Application DAS 1,257,140; in German Unexamined Laid-Open Applications DOS 2,260,303 and 2,264,003; and in U.S. Pat. Nos. 3,519,659 and 3,519,660, whose disclosures are incorporated by reference. It can be seen from these publications which $R_5$ groups can be present in the starting compounds for the process of this invention according to variant (a).

The starting compounds for the process of this invention are prepared according to methods generally known to one skilled in the art, which will be explained in greater detail using as an example typical representatives in the following examples.

Examples of D-homo steroids of general Formula I which can be produced according to the process of this invention are:

11β-hydroxy-3,20-dioxo-D-homo-1,4-pregnadien-21-al

11β,17aα-dihydroxy-3,20-dioxo-D-homo-1,4-pregnadien-21-al

6α-fluoro-11β-hydroxy-3,20-dioxo-D-homo-1,4-pregnadien-21-al

6α-fluoro-11β,17a α-dihydroxy-3,20-dioxo-D-homo-1,4-pregnadien-21-al

9α-fluoro-11β-hydroxy-3,20-dioxo-D-homo-1,4-pregnadien-21-al

9α-fluoro-11β,17a α-dihydroxy-3,20-dioxo-D-homo-1,4-pregnadien-21-al

9α-chloro-11β-hydroxy-3,20-dioxo-D-homo-1,4-pregnadien-21-al

9α-chloro-11β,17aα-dihydroxy-3,20-dioxo-D-homo-1,4-pregnadien-21-al

11β-fluoro-9α-chloro-3,20-dioxo-D-homo-1,4-pregnadien-21-al

11β-fluoro-9α-chloro-17aα-hydroxy-3,20-dioxo-D-homo-1,4-pregnadien-21-al

9α,11β-dichloro-3,20-dioxo-D-homo-1,4-pregnadien-21-al

9α,11β-dichloro-17aα-hydroxy-3,20-dioxo-D-homo-1,4-pregnadien-21-al

11β-hydroxy-3,20-dioxo-6α-methyl-D-homo-1,4-pregnadien-21-al

11β,17aα-dihydroxy-3,20-dioxo-6α-methyl-D-homo-1,4-pregnadien-21-al

11β-hydroxy-3,20-dioxo-6α,17α-dimethyl-D-homo-1,4-pregnadien-21-al

11β,17aα-dihydroxy-3,20-dioxo-6α,17αdimethyl-D-homo-1,4-pregnadien-21-al

6α-fluoro-11β-hydroxy-3,20-dioxo-17α-methyl-D-homo-1,4-pregnadien-21-al

6α-fluoro-11β,17aα-dihydroxy-3,20-dioxo-17α-methyl-D-homo-1,4-pregnadien-21-al

9α-fluoro-11β-hydroxy-3,20-dioxo-17α-methyl-D-homo-1,4pregnadien-21-al

9α-fluoro-11β,17aα-dihydroxy-3,20-dioxo-17α-methyl-D-homo-1,4-pregnadien-21-al

6α,9α-difluoro-11β-hydroxy-3,20-dioxo-17α-methyl-D-homo-1,4-pregnadien-21-al

6α,9α-difluoro-11β,17aα-dihydroxy-3,20-dioxo-17α-methyl-D-homo-1,4-pregnadien-21-al 6α-fluoro-9α-chloro-11β-hydroxy-3,20-dioxo-17α-methyl-D-homo-1,4-pregnadien-21-al 6α-fluoro-9α-chloro-11β,17aα-dihydroxy-3,20-dioxo-17α-methyl-D-homo-1,4pregnadien-21-al, and also the 21-monomethylacetals, 21-monoethylacetals, 21-monobutylacetals, 21,21-dimethylacetals, 21,21-diethylacetals, or 21,21-dibutylacetals of these aldehydes.

The novel D-homo steroids of this invention are pharmacologically active compounds distinguished particularly by an anti-inflammatory activity.

The D-homo steroids of this invention have the advantage that they are metabolized in the body differently from the conventional steroids, so that they often show a more favorable dissociation between the desired anti-inflammatory activity and undesired side effects.

Moreover, the novel D-homo steroids are valuable intermediates suitable especially for the preparation of the novel D-homo steroids of general Formula V

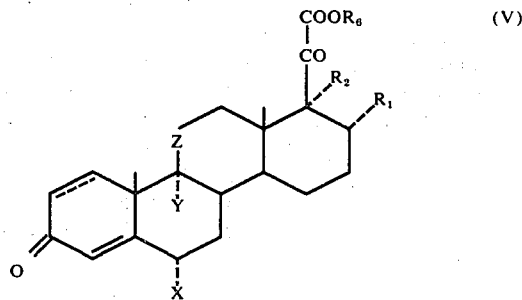

wherein ═, X, Y, Z, R₁, and R₂ have the values given above for Formula I and R₆ is a hydrogen atom or the radical of a physiologically acceptable alcohol, e.g., an n-alkan-1-ol of 1–12 carbon atoms, which compounds are claimed in our concurrently filed application Ser. No. 609,707, whose disclosure is incorporated by reference.

The conditions under which the compounds of general Formula I can be converted into D-homo steroids of general Formula V will be explained with reference to typical representatives in the following examples.

The novel D-homo steroids of general Formulae I and V are pharmacologically effective compounds distinguished particularly in that they possess pronounced topical anti-inflammatory activity and are practically inactive systemically. Moreover, these D-homo steroids are frequently distinguished by a rapid onset of effectiveness, a high intensity of effectiveness, and a long duration of activity. They have an advantageous resorbability and in galenic preparations a relatively good stability. The D-homo steroids of general Formula V are, like those of general Formula I, metabolized in the body in another way than the conventional corticoids with an anti-inflammatory activity.

The novel compounds are suitable, in combination with the vehicles customary in galenic pharmacy, for the local treatment of contact dermatitis, eczema of a great variety of types, neurodermatoses, erythrodermia, burns, pruritus vulvae et ani, rosacea, erythematodes cutaneus, psoriasis, lichen ruber planus et verrucosus, and similar skin diseases.

The special medical preparations are produced in the usual manner by converting the effective agents with suitable additives into the desired form of administration, e.g., solutions, lotions, ointments, creams, or plasters. In the thus-formulated medicinal agents, the concentration of active compound is dependent on the form of application. In case of lotions and ointments, an effective agent concentration of 0.001% to 1% is preferably employed.

Moreover, the novel compounds, optionally in combination with the usual carriers and auxiliary agents, are also well suitable for the preparation of inhalants.

The novel compounds can be employed as topical anti-inflammatory agents in the same manner as the known fluocortolone.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

(a) 130 ml. of methyl iodide is added dropwise to 45 g. of magnesium filings in 1400 ml. of absolute ether. After the magnesium has been dissolved, 2500 ml. of absolute tetrahydrofuran is gradually added thereto, and the mixture is distilled until the distillate has reached a boiling point of 55° C. Then the mixture is cooled to 20° C., 7 g. of copper(I) chloride and a solution of 100 g. of 3β-acetoxy-D-homo-5,17(17a)-dien-20-one in 1000 ml. of absolute tetrahydrofuran are added thereto, and the mixture is stirred for 40 minutes at 20° C.

Thereafter, the mixture is cooled to 0° C.; 230 ml. of 2N sulfuric acid is added dropwise thereto and the mixture is subsequently extracted with ethyl acetate. The extract is washed with sodium thiosulfate solution and water, dried over sodium sulfate, and concentrated under vacuum.

The thus-obtained residue is combined under heating with 300 ml. of pyridine and 150 ml. of acetic anhydride, and the thus-obtained solution is allowed to stand for 16 hours at room temperature. Then, the mixture is poured into ice water, the thus-precipitated product is vacuum-filtered and dissolved in methylene chloride. The methylene chloride solution is washed with dilute sulfuric acid and water, concentrated under vacuum, and the residue is recrystallized from methylene chloride-ethyl acetate. Yield: 75.6 g. of 3β-acetoxy-17α-methyl-D-homo-5-pregnen-20-one, m.p. 212°–213° C.

(b) 30 g. of 3β-acetoxy-17α-methyl-D-homo-5-pregnen-20-one is combined with 300 ml. of glacial acetic acid and heated to 40°–45° C. Within 10 minutes, a solution of 7.9 ml. of bromine in 60 ml. of glacial acetic acid is then added dropwise to the mixture. The latter is allowed to cool, poured into ice-cold potassium acetate solution, the thus-precipitated product is vacuum-filtered, the latter dissolved in ethyl acetate, the ethyl acetate phase is washed with water, evaporated under vacuum at a bath temperature of 40° C. to dryness, and the thus-obtained crude product is 5,6,21-tribromo-3β-acetoxy-17α-methyl-D-homo-pregnan-20-one.

(c) The thus-obtained crude product is combined with 800 ml. of acetone and 80 g. of sodium iodide and stirred under darkness for 16 hours at 20° C. Subsequently the reaction mixture is combined with ice-cold sodium thiosulfate solution; the thus-separated iodide is filtered off, dissolved in ethyl acetate, the ethyl acetate phase is washed with water and concentrated under vacuum.

(d) The residue thus produced is dissolved in 420 ml. of dimethylformamide, mixed with 24 ml. of glacial acetic acid and 42 ml. of triethylamine, and agitated for 4.5 hours under nitrogen at 110° C. Subsequently the reaction mixture is allowed to cool to room temperature, poured into ice-cold sodium chloride solution, and the thus-precipitated product is filtered and dissolved in methylene chloride. The methylene chloride solution is washed with water, dried over sodium sulfate, concentrated under vacuum, and the residue is purified by chromatography over a silica gel column. Yield: 19.5 g. of 3β,21-diacetoxy-17α-methyl-D-homo-5-pregnen-20-one which melts, after recrystallization from ether-pentane, at 135.5° – 137.5° C.

(e) 24.4 g. of 3β,21-diacetoxy-17α-methyl-D-homo-5-pregnen-20-one is dissolved in 250 ml. of methylene chloride, mixed with 250 ml. of 1% methanolic potassium hydroxide solution, and refluxed for 25 minutes. Then, 3 ml. of glacial acetic acid is added to the reaction mixture, the latter is concentrated under vacuum, the residue is taken up in tetrahydrofuran, and the thus-produced solution is concentrated under vacuum. The residue is recrystallized from acetone, thus obtaining 15.8 g. of 3β,21-dihydroxy-17α-methyl-D-homo-5-pregnen-20-one, m.p. 198°–202° C.

(f) 11.7 g. of 3β,21-dihydroxy-17α-methyl-D-homo-5-pregnen-20-one is combined with 150 ml. of dimethylformamide, 20 ml. of acetic anhydride, and 1.1 g. of lead diacetate, and the mixture is agitated for 90 minutes at room temperature. The mixture is then poured into ice-cold sodium chloride solution; the thus-separated product is vacuum-filtered and dissolved in methylene chloride. The methylene chloride extract is washed with water, dried, and concentrated under vacuum. The product thus obtained is recrystallized from methylene chloride-diisopropyl ether, yielding 11.6 g. of 3β-hydroxy-21-acetoxy-17α-methyl-D-homo-5-pregnen-20-one, m.p. 188.5° – 191° C.

(g) 20.5 g. of 3β-hydroxy-21-acetoxy-17β-methyl-D-homo-5-pregnen-20-one is combined with 500 ml. of toluene and 20 ml. of cyclohexanone and heated to the boiling point until several milliliters have been distilled off. Then, a solution of 4.4 g. of aluminum isopropylate in 50 ml. of toluene is added to the mixture; the latter is heated for another hour to such an extent that always some solvent is being distilled off.

The reaction mixture is allowed to cool, diluted with ethyl acetate, the ethyl acetate phase is washed with 1N sulfuric acid and water, and concentrated under vacuum. The residue is purified by chromatography over a silica gel column, recrystallized from acetone-hexane, and the yield is 15.7 g. of 21-acetoxy-17β-methyl-D-homo-4-pregnene-3,20-dione, m.p. 200.5° – 202° C.

(h) A 2-liter Erlenmeyer flask, containing 500 ml. of a nutrient solution, sterilized in an autoclave for 30 minutes at 120° C., made up of 1% of corn steep liquor, 1% of pulverized soybeans, and 0.005% of soybean oil, set to pH 6.2, is inoculated with a lyophilized culture of Curvularia lunata (NRRL 2380) and shaken on a rotary vibrator for 72 hours at 30° C. This subculture is utilized for inoculating a 20-liter fermentor made of stainless steel and filled with 15 l. of a medium, sterilized at 121° C. and 1.1 atmospheres gauge, of 1% of corn steep liquor, 0.5% of glucose, and 0.005% of soybean oil, set to pH 6.2. While adding Silicone SH as antifoam agent, the culture is cultivated for 24 hours at 29° C. under aeration (10 l./min.), a pressure of 0.7 atmosphere gauge, and under agitation (220 r.p.m.). One liter of the culture broth is transferred under sterile conditions into 14 liters of a medium sterilized as above and consisting of 1% of corn steep liquor, 1.25% of pulverized soybeans, and 0.005% of soybean oil and grown under the same conditions. After 6 hours, a solution of 3 g. of 21-acetoxy-17α-methyl-D-homo-4-pregnene-3,20-dione in 150 ml. of dimethylformamide is added thereto.

After a contact time of 23 hours, the content of the fermentor is extracted twice with respectively 10 l. of methyl isobutyl ketone, and the extract is evaporated under vacuum at a bath temperature of 50° C. The residue is washed repeatedly with hexane to remove the silicone oil, and then recrystallized from ethyl acetate while adding activated carbon, thus obtaining 608 mg. of pure 11β,21-dihydroxy-17α-methyl-D-homo-4-pregnene-3,20-dione, m.p. 200.3° C.

(i) A 2-liter Erlenmeyer flask containing 500 ml. of a nutrient solution, sterilized for 30 minutes in an autoclave at 120° C., made up of 1.5% of peptone, 1.2% of corn steep liquor, and 0.2% of MgSO$_4$, set to pH 6.5, is inoculated with a lyophilized culture of Bacillus lentus (ATCC 13 805) and shaken for 24 hours at 30° C. This subculture is then used to inoculate a 20-liter fermentor of stainless steel, containing 15 l. of a liquid nutrient medium, sterilized at 121° C. and 1.1 atmospheres gauge, of 0.2% of yeast extract, 1% of corn steep liquor, and 0.1% of glucose, set to pH 7.0. While adding Silicone SH as the antifoam agent, the mixture is grown at 29° C. under aeration and agitation. After a growth phase of 6 hours, a solution of 3 g. of 11β,21-dihydroxy-17α-methyl-D-homo-4-pregnene-3,20-dione in 150 ml. of dimethylformamide is added thereto.

After a contact time of 15 hours, the content of the fermentor is extracted twice with respectively 10 l. of methyl isobutyl ketone, and the extract is concentrated under vacuum. The residue is washed with hexane to remove the silicone oil and then recrystallized from acetone-diisopropyl ether in the presence of activated carbon. Yield: 2.2 g. of 11β,21-dihydroxy-17α-methyl-D-homo-1,4-pregnadiene-3,20-dione, m.p. 159° C.

(j) One gram of 11β,21-dihydroxy-17α-methyl-D-homo-1,4-pregnadiene-3,20-dione is combined with 250 ml. of methanol and 300 mg. of copper(II) acetate and agitated for 30 minutes while passing air through the mixture. Then, the latter is diluted with methylene chloride, the methylene chloride phase is washed with ammonium chloride solution and water, concentrated under vacuum, and 1.1 g. of 11β-hydroxy-3,20-dioxo-17α-methyl-D-homo-1,4-pregnadien-21-al is obtained as the crude product.

(k) The thus-produced aldehyde is dissolved in 50 ml. of methanol, combined with 160 mg. of potassium cyanide, 1 ml. of glacial acetic acid, and 2 g. of active manganese(IV) oxide, and stirred for 30 minutes at 20° C. The inorganic substance is then removed by vacuum-filtering, mixed with methylene chloride, the filtrates washed with water, concentrated under vacuum, the residue chromatographed over a silica gel column, and the product thus obtained is the methyl ester of 11β-hydroxy-3,20-dioxo-17α-methyl-D-homo-1,4-pregnadien-21-oic acid, m.p. 172°–174° C. (from hexane-acetone).

EXAMPLE 2

(a) A 2-liter Erlenmeyer flask containing 500 ml. of a nutrient solution, sterilized for 30 minutes in an autoclave at 120° C., made up of 1% of corn steep liquor, 1% of pulverized soybeans, and 0.005% of soybean oil, set to pH 6.2, is inoculated with a lyophilized culture of Curvularia lunata (NRRL 2300) and shaken for 72 hours at 30° C. on a rotary vibrator. This subculture is then employed to inoculate a 20-liter fermentor containing 15 l. of a medium, sterilized at 121° C. and 1.1 atmospheres gauge, made up of 1% of corn steep liquor, 0.5% of glucose, and 0.005% of soybean oil, set to pH 6.2. under the addition of Silicone SH as the antifoam agent, the culture is cultivated at 29° C. under aeration (10 l./min), a pressure of 0.7 atmospheres gauge, and under agitation (220 r.p.m.) for 24 hours. One liter of the culture broth is transferred under sterile conditions into 14 l. of a medium sterilized as above and consisting of 1% of corn steep liquor, 1.25% of pulverized soybeans, and 0.005% of soybean oil, and is grown under the same conditions. After 6 hours, a solution of 6 g. of 21-acetoxy-D-homo-4-pregnene-3,20-dione in 300 ml. of dimethyl sulfoxide is added thereto.

After a contact time of 44 hours, the content of the fermentor is extracted under agitation twice with respectively 10 l. of methyl isobutyl ketone, and the extract is evaporated under vacuum at a bath temperature of 50° C. The residue is once again washed with hexane to remove the silicone oil and then converted by digestion with acetone-isopropyl ether into a crystalline crude product (3.1 g.) which is used in this form for the subsequent dehydrogenation.

A sample of the crude product is recrystallized from acetone-ether to obtain 11β,21-dihydroxy-D-homo-4-pregnene-3,20-dione, m.p. 188/192°–195° C.

(b) A 2-liter Erlenmeyer flask containing 500 ml. of a nutrient solution, sterilized for 30 minutes at 120° C. in an autoclave and made up of 1.5% of peptone, 1.2% of corn steep liquor, and 0.2% of MgSO$_4$, set to pH 6.5, is inoculated with a lyophilized culture of Bacillus lentus (ATCC 13 805) and shaken for 24 hours at 30° C. This subculture is then used to inoculate a 20-liter fermentor containing 15 l. of a liquid nutrient medium, sterilized at 121° C. and 1.1 atmospheres gauge, made up of 0.2% of yeast extract, 1% of corn steep liquor, and 0.1% of glucose, set to pH 7.0. With the addition of Silicone SH as the antifoam agent, the culture is grown at 29° C. under aeration and agitation. After a growth phase of 6 hours, a solution of 6 g. of 11β,21-dihydroxy-D-homo-4-pregnene-3,20-dione in 100 ml. of dimethylformamide is added thereto.

After a contact time of 42 hours, the content of the fermentor is extracted twice with respectively 10 l. of methyl isobutyl ketone, and the extract is evaporated under vacuum. The residue is washed with hexane to remove the silicone oil and, after treatment with active C in methanolic solution recrystallized twice from acetone-ether to obtain 3 g. of 11β,21-dihydroxy-D-homo-1,4-pregnadiene-3,20-dione, m.p. 170/173°–174° C.

(c) 800 mg. of 11β,21-dihydroxy-1,4-pregnadiene-3,20-dione is dissolved in 8ml. of dimethylformamide, combined with 1.6 ml. of acetic anhydride and 112 mg. of lead diacetate, and agitated for 2 hours at room temperature. Then, the mixture is precipitated into ice water, the product is vacuum-filtered, washed with water, and dried. Recrystallization from acetone-hexane yields 820 mg. of 11β-hydroxy-21-acetoxy-D-homo-1,4-pregnadiene-3,20-dione, m.p. 192°–193° C.

(d) 760 mg. of 11β-hydroxy-21-acetoxy-D-homo-1,4-pregnadiene-3,20-dione is dissolved in 4 ml. of dimethylformamide and 0.76 ml. of pyridine, and 0.38 ml. of methanesulfonic acid chloride is added dropwise thereto. The mixture is thereafter stirred for 1.5 hours at 80° C., then cooled to 20° C, poured into ice water, and the thus-precipitated product is vacuum-filtered, washed with water, and dried under vacuum. After recrystallization from acetone-hexane, the yield is 650 mg. of 21-acetoxy-D-homo-1,4,9(11)-pregnatriene-3,20-dione, m.p. 135°–136° C.

(e) 374 mg. of 21-acetoxy-D-homo-1,4,9(11)-pregnatriene-3,20-dione is dissolved in 9 ml. of tetrahydrofuran; 535 mg. of N-bromosuccinimide is added thereto, the mixture is cooled to 0°–5° C., and 3.3 ml. of 1N perchloric acid is added dropwise. The mixture is then stirred for 30 minutes at 20° C., poured into ice-cold sodium sulfite solution, the precipitated product is vacuum-filtered and dissolved in methylene chloride. The methylene chloride solution is washed with water and concentrated under vacuum, thus obtaining 520 mg. of crude 21-acetoxy-9α-bromo-11β-hydroxy-D-homo-1,4-pregnadiene-3,20-dione.

(f) 520 mg. of the crude bromohydrin is heated in 25 ml. of ethanol with 1.25 g. of potassium acetate for 1 hour under reflux. The reaction mixture is poured into ice water, the thus-precipitated product is vacuum-filtered, washed with water, and dried under vacuum. After recrystallization from cyclohexane, 320 mg. of 21-acetoxy-9β,11β-epoxy-D-homo-1,4-pregnadiene-3,20-dione is obtained, m.p. 152°–153° C.

(g) 320 mg. of 21-acetoxy-9β,11β-epoxy-D-homo-1,4-pregnadiene-3,20-dione is dissolved in 2 ml. of dimethylformamide and added to a mixture of 2 ml. of dimethylformamide and 2 ml. of hydrogen fluoride, cooled to −20° C. The mixture is stirred for 19 hours at room temperature and then poured into water which contains potassium acetate. The precipitated product is vacuum-filtered, washed with water, dried, and recrystallization from acetone yields 169 mg. of 9α-fluoro-11β-hydroxy-21-acetoxy-D-homo-1,4-pregnadiene-3,20-dione, m.p. 227°–228° C.

(h) Three grams of 9α-fluoro-11β-hydroxy-21-acetoxy-D-homo-1,4-pregnadiene-3,20-dione is combined with 12 ml. of methanol and 12 ml. of methylene chloride, cooled to −5° C., and a solution of 0.18 g. of potassium hydroxide in 6 ml. of methanol is added dropwise thereto. The mixture is then stirred for another 60 minutes at 0° C., neutralized with acetic acid, diluted with methylene chloride, the methylene chloride phase washed with water, concentrated under vacuum, and the residue is recrystallized from hexane-acetone, thus obtaining 2.4 g. of 9α-fluoro-11β,21-dihydroxy-D-homo-1,4-pregnadiene-3,20-dione, m.p. 197°–199° C. (i) under the conditions of Example 1(j), one gram of 9α-fluoro-11β,21-dihydroxy-D-homo-1,4-pregnadiene-3,20-dione is reacted, yielding 1.1 g. of 9α-fluoro-11β-hydroxy-3,20-dioxo-D-homo-1,4-pregnadien-21-al as the crude product.

(j) Under the conditions of Example 1(k), but with the use of butanol in place of methanol, one gram of 9α-fluoro-11β-hydroxy-3,20-dioxo-D-homo-1,4-pregnadien-21-al is reacted, yielding the butyl ester of 9α-fluoro-11β-hydroxy-3,20-dioxo-D-homo-1,4-pregnadien-21-oic acid, m.p. 121°–123° C.

EXAMPLE 3

(a) 11β,21-Dihydroxy-D-homo-1,4-pregnadiene-3,20-dione is reacted under the conditions of Example 1(j), thus obtaining 11β-hydroxy-D-homo-1,4-pregnadien-21-al as the crude product.

(b) The thus-obtained aldehyde is reacted under the conditions of Example 2(j), obtaining the butyl ester of 11β-hydroxy-3,20-dioxo-D-homo-1,4-pregnadien-21-oic acid, m.p. 103°–104.5° C.

EXAMPLE 4

(a) A Grignard solution (prepared from 21 g. of magnesium filings, 72.5 g. of methyl iodide, and 1000 ml. of ether) is diluted with 1000 ml. of absolute tetrahydrofuran and distilled until the distillate has reached a boiling point of 50° C. The thus-obtained suspension is then cooled to 20° C., combined with 4 g. of copper(I) chloride and a solution of 50 g. of 3β-hydroxy-D-homo-5,17(17a)-pregnadien-20-one in 2000 ml. of absolute tetrahydrofuran, and the mixture is agitated for 20 minutes at room temperature. The reaction mixture is worked up as usual, the crude product is recrystallized from acetone, and the yield is 32.5 g. of 3β-hydroxy-17α-methyl-D-homo-5-pregnen-20-one, m.p. 207°–209° C.

(b) 10 g. of 3β-hydroxy-17β-methyl-D-homo-5-pregnen-20-one is suspended in 1000 ml. of tetrahydrofuran and combined dropwise with a solution of 3.6 ml. of bromine in 10 ml. of glacial acetic acid (duration about 15 minutes). Subsequently, the reaction mixture is worked up as described in Example 1(b), thus obtaining 3β-hydroxy-5,6,21-tribromo-17α-methyl-D-homo-pregnan-20-one as a crude product.

(c) The thus-obtained tribromo derivative is reacted under the conditions described in Example 1(c) with 300 ml. of acetone and 35 g. of sodium iodide and then worked up, obtaining the 21-iodide compound as the crude product.

(d) The 21-iodide is dissolved in 140 ml. of dimethylformamide, combined with 8 ml. of glacial acetic acid and 14 ml. of triethylamine, and stirred for 11 hours at 90° C. The reaction mixture is worked up as described in Example 1(d), thus obtaining 4.4 g. of 3β-hydroxy-21-acetoxy-17α-methyl-D-homo-5-pregnen-20-one, melting at 188°–190° C. after recrystallization from methylene chloride-diisopropyl ether.

(e) 470 mg. of N-bromosuccinimide is introduced into a solution, cooled to −30° C., of 3 ml. of hydrogen fluoride and 3 ml. of dimethylformamide. Then, a pre-cooled solution of 1 g. of 3β-hydroxy-21-acetoxy-17α-methyl-D-homo-5-pregnen-20-one in 8 ml. of methylene chloride is added to the mixture in incremental portions; the mixture is stirred for 10 minutes at −30° C., poured into ice-cold potassium bicarbonate solution, and extracted with methylene chloride. The methylene chloride phase is washed with water, evaporated to dryness under vacuum, the residue recrystallized from acetone, and the yield is 627 mg. of 6β-fluoro-5α-bromo-3β-hydroxy-21-acetoxy17α-methyl-D-homo-5α-pregnan-20-one, m.p. 168.5° C. (decomposition).

(f) 300 mg. of 6β-fluoro-5α-bromo-3β-hydroxy-21-acetoxy-17α-methyl-D-homo-5α-pregnan-20-one is combined, in 10 ml. of acetone, dropwise with 0.19 ml. of Jones reagent (containing, per liter, 267 g. of chromium(VI) oxide, 230 ml. of concentrated sulfuric acid in water); the mixture is agitated for 10 minutes at 20° C. Thereafter, the mixture is poured into ice water, the separated product is vacuum-filtered, taken up in methylene chloride, the methylene chloride phase is washed with water and concentrated under vacuum. Yield: 298 mg. of 6β-fluoro-5α-bromo-21-acetoxy-17α-methyl-D-homo-5α-pregnane-3,20-dione as the crude product.

(g) This crude product is dissolved in 5 ml. of glacial acetic acid and agitated for 3 hours at 30° C. Then, the mixture is combined with 100 mg. of sodium acetate, stirred for 10 minutes at 30° C., poured into ice water; the thus-separated product is vacuum-filtered and taken up in methylene chloride. The methylene chloride phase is washed with water, concentrated under vacuum, and the residue is recrystallized from acetone, thus obtaining 250 mg. of 6α-fluoro-21-acetoxy-17α-methyl-D-homo-4-pregnene-3,20-dione.

(h) Under the conditions described in Example 1(h), 3 g. of 6α-fluoro-21-acetoxy-17α-methyl-D-homo-4-pregnene-3,20-dione is fermented with Curvularia lunata, worked up, and the product is 6α-fluoro-11β,21-dihydroxy-17α-methyl-D-homo-4-pregnene-3,20-dione.

(i) Under the conditions described in Example 1(i), 1.2 g, of 6α-fluoro-11β,21-dihydroxy-17α-methyl-D-homo-4-pregnene-3,20-dione is reacted with a culture of Bacillus lentus, worked up, and the product is 6α-fluoro-11β,21-dihydroxy-17α-methyl-D-homo-1,4-pregnadien-3,20-dione.

(j) Under the conditions of Example 1(j), 6α-fluoro-11β,21-dihydroxy-17α-methyl-D-homo-1,4-pregnadien-3,20-dione is reacted, thus obtaining 6α-fluoro-11β-hydroxy-3,20-dioxo-17α-methyl-D-homo-1,4-pregnadien-21-al as a crude product.

(k) Under the conditions of Example 2(j), 6α-fluoro-11β-hydroxy-3,20-dioxo-17α-methyl-D-homo-1,4-pregnadien-21-al is reacted, yielding the butyl ester of 6α-fluoro-11β-hydroxy-3,20-dioxo-17α-methyl-D-homo-1,4-pregnadien-21-oic acid.

EXAMPLE 5

(a) One gram of 17aα,21-dihydroxy-D-homo-4-pregnene-3,20-dione (DOS 2,314,592) is dissolved in 200 ml. of methanol and combined with 250 mg. of copper-(II) acetate. For 50 minutes, air is conducted through the mixture; then the latter is stirred into water and extracted with methylene chloride. The methylene chloride phase is washed, dried, concentrated under vacuum, and the product is 1.03 g. of 17aα-hydroxy-D-homo-4-pregnen-21-al in crude form.

(b) 510 mg. of the thus-produced aldehyde is dissolved in 18.3 ml. of chloroform and 11.5 ml. of methanol, combined with 0.63 ml. of glacial acetic acid and 115 mg. of potassium cyanide, and agitated for 50 minutes at 20° C. The mixture is then diluted with methylene chloride, the methylene chloride phase is washed, concentrated under vacuum, and the residue chromatographed over a silica gel column, yielding 157 mg. of the methyl ester of 17aα-hydroxy-D-homo-4-pregnen-21-oic acid, m.p. 171°–172° C. (from hexane-acetone).

EXAMPLE 6

(a) One gram of 11β,17aα,21-trihydroxy-D-homo-1,4-pregnadiene-3,20-dione is dissolved in 20 ml. of methanol and combined with 300 mg. of copper(II) acetate. Under agitation, air is conducted through the mixture for 2 hours, diluted with 200 ml. of chloroform, the chloroform phase is washed and concentrated under vacuum, and the crude product thus obtained is 11β,17aα-dihydroxy-D-homo-1,4-pregnadien-21-al which melts at 136°–140° C. after recrystallization from methanol.

(b) The thus-prepared aldehyde is dissolved in 8 ml. of absolute methanol and 75 ml. of absolute acetonitrile, the solution is combined, in succession, with 3 g. of anhydrous calcium carbonate, 1.6 ml. of glacial acetic acid, 2 g. of active manganese(IV) oxide, and 0.352 g. of potassium cyanide. The mixture is agitated for 3 minutes at room temperature, then vacuum-filtered by way of a sinter vacuum filter into 300 ml. of ice water, and the residue is washed with chloroform. The organic phase is separated, the aqueous phase is extracted with chloroform, the chloroform phases are combined, washed, and concentrated under vacuum. The residue is chromatographed over silica gel, thus obtaining 570 mg. of the butyl ester of 11β,17aα-dihydroxy-3,20-dioxo-D-homo-1,4-pregnadien-21-oic acid, m.p. 110°–115° C. (from diisopropyl ether).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A D-homo steroid of the formula

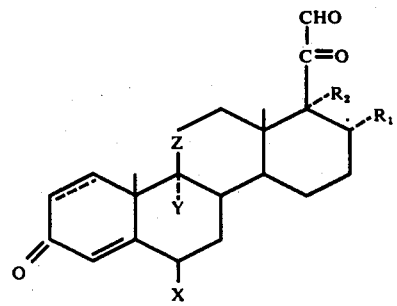

wherein
==== is a single bond or a double bond;
X is a hydrogen atom, a fluorine atom or methyl;
Y is a hydrogen atom, a fluorine atom or a chlorine atom;
Z is methylene, carbonyl, β-hydroxymethylene, β-alkanoyloxymethylene or, when Y is a chlorine atom, also β-fluoromethylene or β-chloromethylene;
$R_1$ is a hydrogen atom or methyl;
$R_2$ is a hydrogen atom, hydroxy, or alkanoyloxy;

alkanoyl in each instance being of 1–8 carbon atoms.

2. A compound of claim 1, wherein ═══ is a double bond.

3. A compound of claim 1, wherein X is H.

4. A compound of claim 1, wherein Y is H.

5. A compound of claim 1, wherein Z is β-hydroxymethylene.

6. A D-homo steroid of the formula

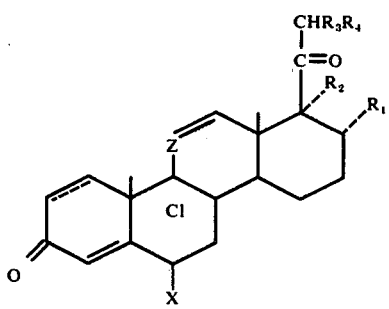

wherein ═══ is a single or a double bond; X is a hydrogen atom, a fluorine atom or methyl; Z is β-fluoromethylene or β-chloromethylene; $R_1$ is a hydrogen atom or methyl; $R_2$ is a hydrogen atom, hydroxy or alkanoyloxy; and one of $R_3$ and $R_4$ is a hydrogen atom and the other is hydroxy or lower alkoxy or collectively $R_3$ and $R_4$ are an oxygen atom, alkanoyl in each instance being of 1–8 carbon atoms.

7. A compound of claim 1, wherein $R_2$ is H.

8. 11β-Hydroxy-3,20-dioxo-17α-methyl-D-homo-1,4-pregnadien-21-al, a compound of claim 1.

9. 9α-Fluoro-11β-hydroxy-3,20-dioxo-D-homo-1,4-pregnadien-21-al, a compound of claim 1.

10. 11β-Hydroxy-3,20-dioxo-D-homo-1,4-pregnadien-21-al, a compound of claim 1.

11. 6α-Fluoro-11β-hydroxy-3,20-dioxo-17α-methyl-D-homo-1,4-pregnadien-21-al, a compound of claim 1.

12. 17aα-Hydroxy-D-homo-4-pregnen-21-al, a compound of claim 1.

13. 11β,17aα-Dihydroxy-D-homo-1,4-pregnadien-21-al, a compound of claim 1.

14. A pharmaceutical composition adapted for topical administration comprising an anti-inflammatory effective amount per unit dosage of a D-homo steroid of claim 1 in admixture with a pharmaceutically acceptable carrier.

15. A method for the treatment of topical inflammations which comprises administering to the inflammed area an anti-inflammatorily effective amount of a D-homo steroid, of claim 1.

* * * * *